United States Patent [19]

Iams

[11] Patent Number: 5,452,728
[45] Date of Patent: Sep. 26, 1995

[54] SOFT TISSUE SUPPORT SYSTEM

[75] Inventor: John Iams, Poway, Calif.

[73] Assignee: Superspine, Inc., Poway, Calif.

[21] Appl. No.: 263,516

[22] Filed: Jun. 22, 1994

Related U.S. Application Data

[62] Division of Ser. No. 18,348, Feb. 16, 1993, which is a continuation of Ser. No. 672,041, Mar. 18, 1991, which is a division of Ser. No. 318,642, Mar. 2, 1989, Pat. No.5,070,865.

[51] Int. Cl.⁶ .................................................. A61G 15/00
[52] U.S. Cl. ................................................ 128/845; 5/630
[58] Field of Search ........................... 128/845, 846; 606/237–242; 5/636, 637, 640, 643, 630

[56] References Cited

U.S. PATENT DOCUMENTS

| | | | |
|---|---|---|---|
| 2,180,775 | 11/1939 | Stevens | 606/237 |
| 2,556,629 | 6/1951 | O'Brien | 5/643 |
| 3,140,497 | 7/1964 | Carswell | 5/643 |
| 3,337,883 | 8/1967 | Allison | 5/643 |
| 4,321,890 | 3/1982 | Lange | 128/845 |
| 4,475,542 | 10/1984 | Brossard | 606/240 |
| 4,785,801 | 11/1988 | Speece | 606/240 |
| 4,805,603 | 2/1989 | Cumberland | 602/13 |
| 5,222,979 | 6/1993 | Brossard | 606/240 |

Primary Examiner—Michael A. Brown
Attorney, Agent, or Firm—Gregory Garmong

[57] ABSTRACT

A set of supportive pivots and an approach for their use permit individuals to administer a wide variety of types of motion therapy and conditioning for the spinal, rib, and skull regions. Singly, and in various combinations, the pivots support the lumbar, thoracic, cervical, cranial, and shoulder regions, when a person lies on the back or stomach on an accommodative support surface, with the spine unloaded. Most of the pivots are contoured with a longitudinal fulcrum parallel to the spine. A person lying on an individual pivot or pairs of the pivots can apply a mild pivotal traction to the spine by properly positioning the pivots and shifting weight to create traction and self mobilization. Another set of pivots can be placed under the shoulders when the person lies on the stomach, to stretch the chest musculature, to mobilize the ribs and breastbone joints, and to exercise the shoulder girdle.

5 Claims, 5 Drawing Sheets

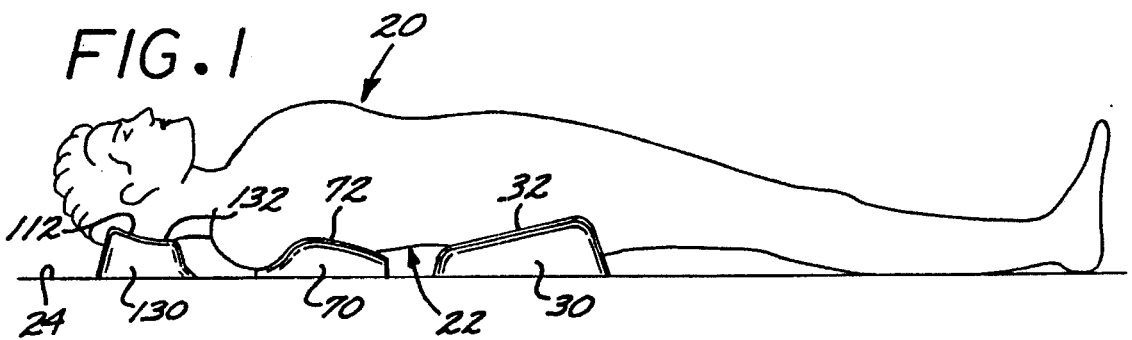
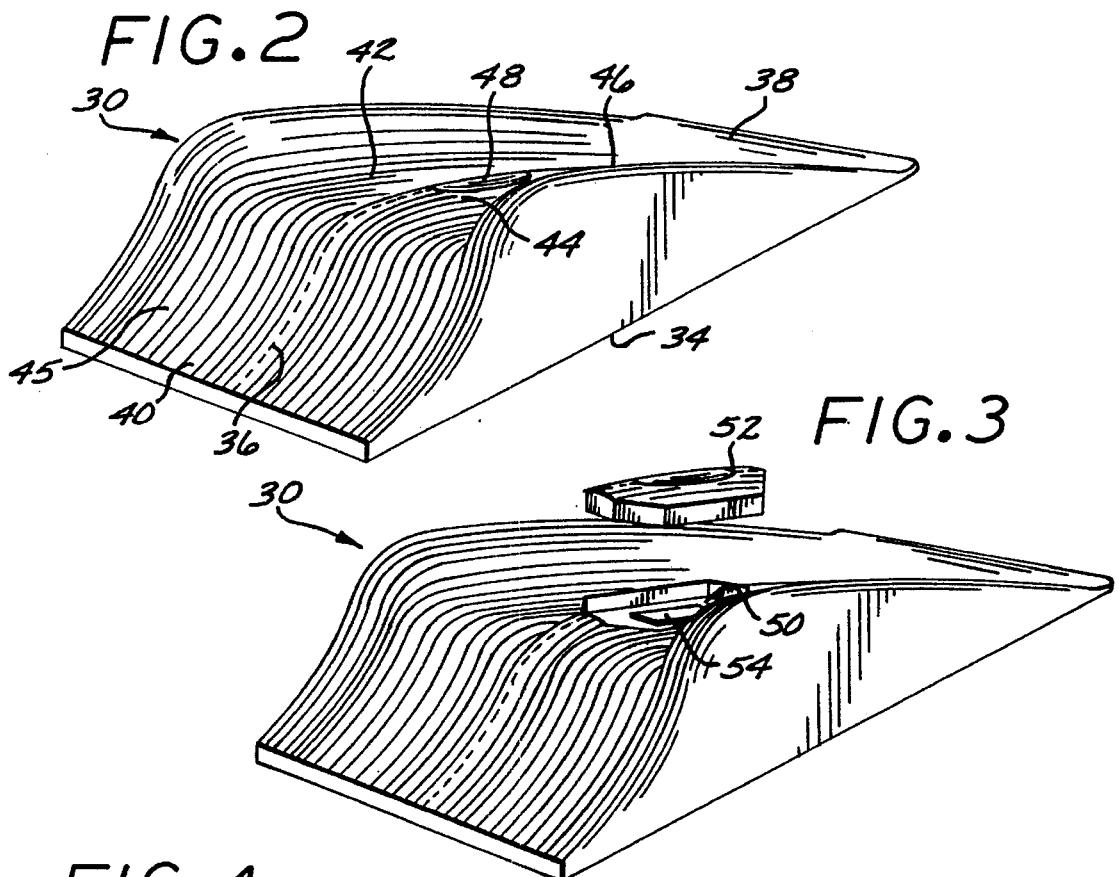
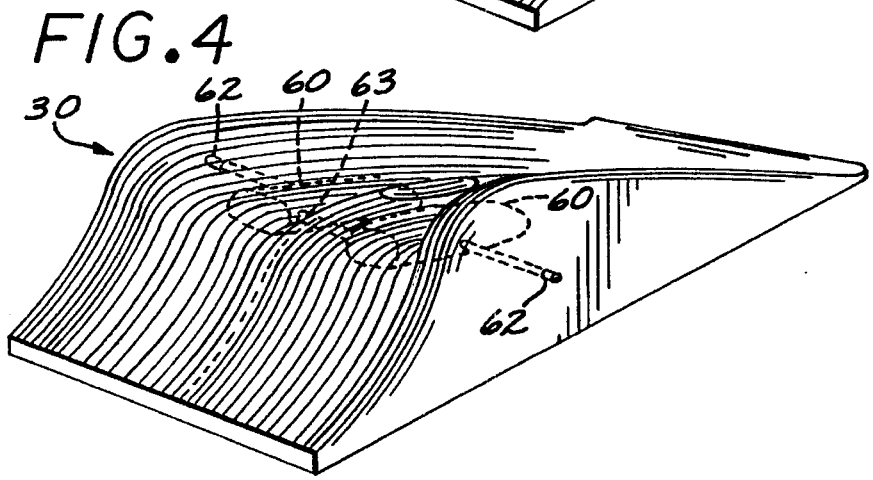

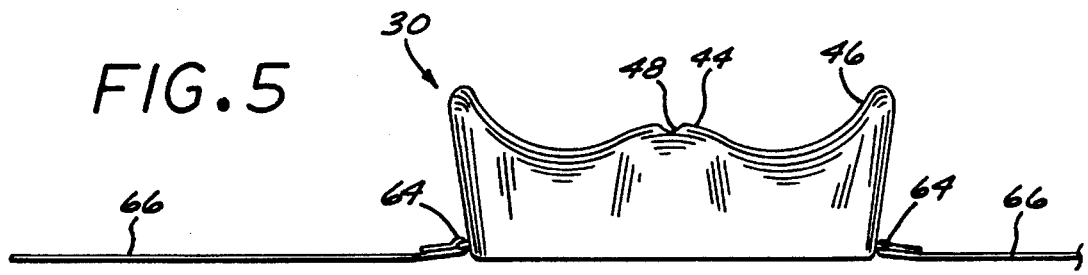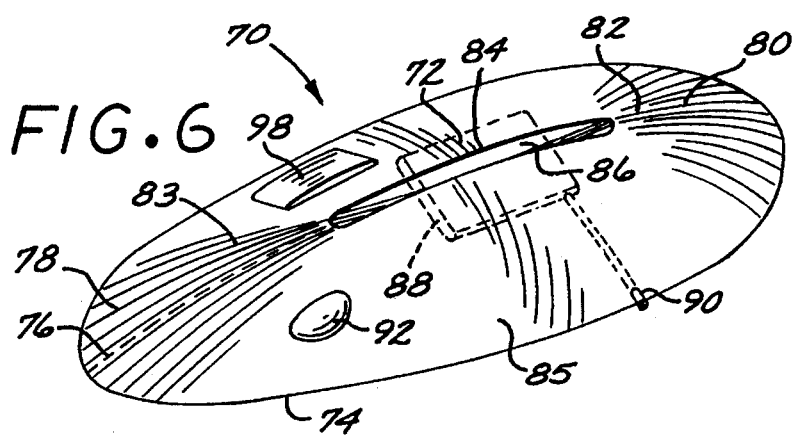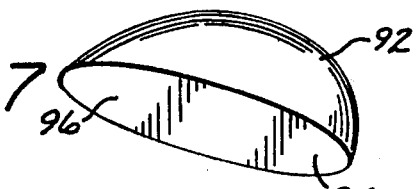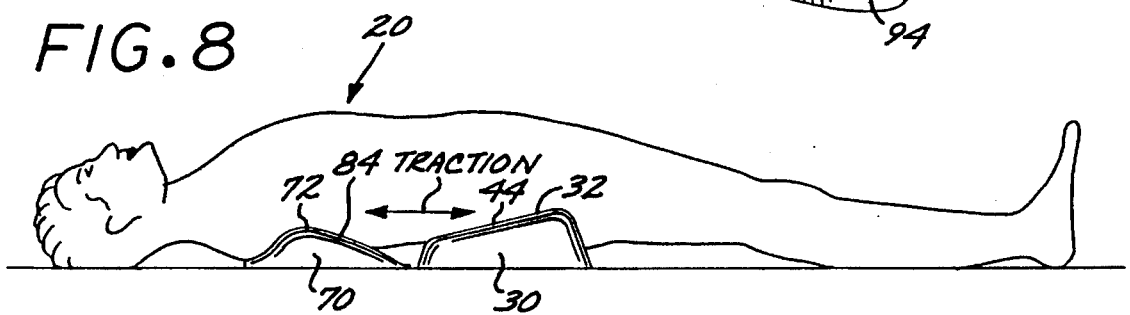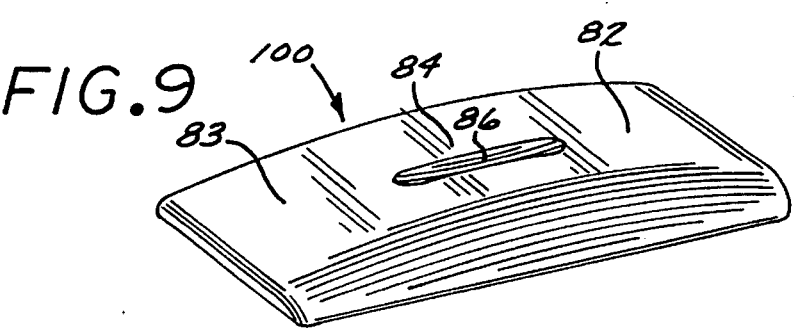

SOFT TISSUE SUPPORT SYSTEM

This is a division of application Ser. No. 08/018,348, filed Feb. 16, 1993, which in turn is a continuation of application Se. No. 07/672,041, filed Mar. 18, 1991, which in turn is a division of application Ser. No. 07/318,642 filed Mar. 2, 1989 now U.S. Pat. No. 5,070,865. Priority of all of these prior applications is claimed.

BACKGROUND OF THE INVENTION

This invention relates to the care of the spine and musculature of the human body, and, more particularly, to a passive technique with gravity assist for achieving such care.

Health is of concern to most persons, and recently there has been a great focus on cardiovascular conditioning, weight control, the benefits of proper diet, and other considerations of achieving overall good health. For example, people may attend health clubs, jog, undertake particular types of diets, and many other self-directed activities by way of taking care of themselves. These activities are intended to maintain the body in good health, and also recover from or reduce the effect of problems that may have been experienced.

There has been, however, relatively little attention paid to maintaining the health of the spine and its related structural environs including the ribs and rib attachments. This general lack of attention to the health of the spine is notwithstanding the fact that almost everyone will experience some sort of neck, back, headache, or other problem whose origins can be traced to the spine. Thus, for example, lower back pain often has its origin in problems with the thoracic spine and rib attachments.

The changing life styles of many persons are particularly conducive to a gradual development of problems related to the spine. For example, sitting at a desk or terminal for long periods can develop a condition of muscular fatigue that gradually causes the person's posture to be pulled forward. The body compensates in an effort to retain an erect posture, but the continuing tension may eventually cause permanent deformities and pain that can become so severe as to be disabling, or, at the very least, sufficiently uncomfortable to reduce productivity and creativity.

Complaints about spinal and back pain are among the most common expressions of health concern, but until the pain becomes disabling most persons simply learn to live with the pain or treat it with pain killers that reduce the pain but do nothing about the problem. Once spinal-related problems have reached a severe stage that is too serious to ignore, sufferers can be treated by physical therapists, chiropractors, or surgeons. In many cases some degree of relief is possible, but the relief may be short lived after the treatment is ended. Moreover, many persons have a natural reluctance to seek professional help until the problems again become unbearable.

Although there are many approaches for self-directed conditioning of the heart and other parts of the body, there has been little proposed in the way of conditioning and self-treatment techniques for the spine that a person may use by himself. That is, after the person suffering severe problems has been treated by the health care professional, there is little that he can do to aid himself until the next visit. Also, there is little by way of self-conditioning equipment that the concerned person may use throughout his life to maintain an original state of good spinal health, or use to provide self-treatment for minor problems before they become major problems.

Thus, there is a need for an approach by which an original state of good spinal joint posture and musculature health may be maintained, or by which minor problems may be self-treated before they progress to become disabling and so severe as to require professional treatment. Such an approach must be medically sound in the sense that the treatment is medically beneficial, and desirably is easy and convenient to use so that the person is encouraged to use the approach on a regular basis as part of a conditioning program. The approach desirably would also be inexpensive to implement and maintain. The present invention fulfills this need, and further provides related advantages.

SUMMARY OF THE INVENTION

The present invention provides an apparatus and process useful in conditioning and treating the body for the prevention and alleviation of spinal problems and other problems arising from spinal related areas such as the ribs, skull, breastbone, etc. The treatment follows and is in accordance with procedures used by physical therapists, osteopaths, and other professionals in this field, and is medically sound. The treatment "feels good" to the user, a critical consideration for an approach that is intended in part to be used over the lifetime of the person to maintain good health. The apparatus is relatively inexpensive to purchase and maintain. It is also portable, and can be taken to the workplace or on travel. The apparatus and treatment are convenient to use in either a regular conditioning or a therapy program, and may be undertaken at the same time that the user is performing other activities such as reading or watching television. Some movement may be involved, and to a certain extent the procedure is dynamic in that pivotal therapy may be applied. However, the treatment is not physically rigorous and does not require large expenditures of effort. Thus, it can be utilized when the person is aged, infirm, partially debilitated, or tired from work or other exercise.

The invention provides for particular pivots and pads to achieve the ends of the invention. In accordance with the invention, a lumbar support pivot compatible with the anatomy of a person lying upon the pivot comprises a pad made of a firmly compliant material, the pad including a longitudinally upwardly inclined lumbar support surface longitudinally contoured to fit to the thoraco-lumbar region; a lordotic fulcrum continuous with the top end of the lumbar support surface, the fulcrum conforming longitudinally to the lordotic region and having a longitudinally extending central spinal depression adapted to receive the spinous processes, the fulcrum having sides that slope laterally downwardly from the region of the central spinal depression; a sacral support surface that is longitudinally downwardly inclined from the fulcrum, and extends laterally over the width of the sacral region; and a pair of raised side support surfaces contoured upwardly from the lateral margin of the fulcrum and the lateral margin of the sacral support surface, and shaped to the pelvis. In another form, a lumbar support pivot comprises a pad made of a firmly compliant material having a longitudinal fulcrum adapted for fitting the lumbar region of the spine of a person lying thereon, and further having raised side portions that restrain the lateral movement of the pelvis of the person.

A thoracic support pivot compatible with the anatomy of a person lying upon the pivot comprises a pad made of a firmly compliant material and having an upper support surface having a longitudinally upwardly sloping shape; a thoracic fulcrum continuous with the upper support surface at its highest extent, the fulcrum being longitudinally ridged to press against the thoracic region of the spine and having a longitudinally extending depression therein for receiving the spinous processes, the fulcrum having a transverse width less than that of the scapulae such that the thoracic region of the spine is supported upon the fulcrum to permit the scapulae to relax downwardly; a lower support surface continuous with the end of the fulcrum remote from the upper support surface and having a longitudinally downwardly sloping shape; and a pair of convex side surfaces extending downwardly from the lateral margin of the upper support surface, the fulcrum, and the lower support surface. In another embodiment, a thoracic support pivot that supports a person upon a support surface, comprises a pad made of a firmly compliant material having a longitudinal fulcrum adapted for pressing against the thoracic region of the spine, and further having a transverse width less than the width between the shoulder blades such that the thoracic region of the spine is supported upon the fulcrum with the shoulder blades free to relax downwardly.

A cervical support pivot compatible with the anatomy of a person lying upon the pivot comprises a pad made of a firmly compliant material, the pad having an upwardly extending upper surface; a fulcrum continuous with the top of the upper surface, the fulcrum being laterally upwardly curved from its central region with protrusions thereon and shaped to fit the occipital region of the skull; a cervical support surface sloping longitudinally downwardly from the fulcrum and having a longitudinal convex shape to conform to the upper cervical region; and a pair of side walls laterally adjacent the margin of the fulcrum and the margin of a portion of the cervical support surface, the side walls extending upwardly and having at the end adjacent the fulcrum a raised protrusion positioned to press against the upper end of the sternocleidomastoid muscle, and having at the end remote from the fulcrum a protrusion adapted to press against the upper trapezius and first rib. A cervical support pivot comprises a pad made of a firmly compliant material having a longitudinal fulcrum and a cervical support surface shaped to fit the cervical region of the spine, and further having raised side portions on the lateral margins of the fulcrum and the cervical support surface.

An occipital support pivot compatible with the anatomy of a person lying upon the pivot comprises a pad made of a firmly compliant material having an upwardly extending upper surface; a fulcrum continuous with the top of the upper surface, the fulcrum being laterally upwardly curved from its central region and shaped to fit the occipital region of the skull; a lower surface sloping longitudinally downwardly from the fulcrum; and an occipital support protrusion extending upwardly from the fulcrum and dimensioned to contact a selected location on the occiput. In another form, an occipital support pivot comprises a pad made of a firmly compliant material and having a longitudinal fulcrum adapted for fitting the occipital region.

A shoulder support pad comprises a body made of a rigid material in the form of a U; and a compliant foam material filling the center of the U, the upper surface of the foam material extending longitudinally from the top of the first leg to the top of the second leg, the upper surface of the foam material further sloping laterally downwardly. In a preferred form, the body is asymmetric with a first leg of the U shaped body extending upwardly to a height greater than the second leg, and there is an end piece of lateral width greater than the width of the body and joined to the body adjacent the first leg.

Each pivot of the invention may be used singly to support the particular region of the spine, neck, or skull for which it is particularly adapted. The pivots may also be used in combination, as to apply a mild traction to the spine.

In accordance with the invention, apparatus for applying therapy to the spine of a person in a longitudinal direction along the spine comprises pivot means for supporting a portion of the spine of the person above a horizontal support surface upon which the person lies, the pivot means including a first pivot and a second pivot, each pivot being made of a firmly compliant material, the first pivot having a raised longitudinal fulcrum of sufficient height to support a region of the spine of the person on the fulcrum with the person lying on the back on a horizontal support surface, without the portion of the spine lying between the two pivots resting upon the support surface. Of course, more than two pivots may be used together to achieve further therapy and shaping of the back.

During the professional treatment of some back, spine, and posture problems, in many instances two types of force are repeatedly employed to provide relief from pain and discomfort. Spinal traction is used in instances where the spine has become injured or stiff, or where spinal disks have become displaced from their proper positions between the vertebrae. A constant strong or intermittent force separating the vertebrae is used to relieve deep muscle pain and other continuing pain.

However, once the patient leaves the professional's office, continuing self-treatment may be difficult. A machine for applying spinal traction is both expensive and cumbersome. Gravity boots, widely used for several years, are not suitable for use by the infirm and elderly, and may be dangerous because of the possibility of falls or other problems. The application of pressure to relieve pain is certainly possible if the sufferer has the assistance of a masseuse, patient family member, or the like, but continuing relief is difficult to obtain. It is not practical for the person needing relief to manually apply pressure and manipulation to his own back. Thus, it is typically the situation that the person suffering from these types of problems can obtain a degree of relief only during visits to the professional, which relief may persist for only a limited time thereafter.

The pivots of the present invention provide a basis for self mobilization of the spine and associated structure, such as ribs and vertebrae, to achieve self-treatment of back and spine problems, and also for self-conditioning and development of the back and spine to avoid such problems. The pivots of the present invention, when used singly or in particular combinations, permit the user to apply mild spinal tractions to selected regions of his or her own spine, to shape the spine and the resulting body posture, and to apply mild pain relieving pressure to the spine, ribs, and other laterally adjacent regions of the back.

The pivots of the invention are preferably used in supporting a person in a horizontal or lying position. Some treatments for the spine and back are used with the person in other positions, as a standing or sitting position. In such an upright position, the spine is under lead, typically a compressive lead from the weight of the upper part of the body. A feature of the present approach is the application of shaping and pressure to the back with the spine unloaded, and the most direct approach to providing such loading is with the person lying on the back on top of one or more pivots.

Each of the pivots of the invention incorporates a raised portion or fulcrum, wherein the thickness of the pivot increases from at least one end to a high point that may be near the center of the pivot or near the other end. In use, the fulcrum of the pivot is used in a manner consistent with the conventional concept of a fulcrum, that is, a pivot point for the support and operation of a lever. The person lies on the pivot with the fulcrum contacting a point to which pressure is to be applied. In the case of the lumbar and thoracic support pivots, the pivots shape the back to the correct shape for treatment. With a slight shifting of weight, the person can move the center of gravity of the supported portion of the body from one side of the fulcrum to the other, producing a rocking motion that causes the pressure to change in a manner resembling a manual massage. The result is a beneficial deep and changing self-created and controlled pressure and pivotal therapy applied to a selected location of the back, with the spine unloaded and in the correct shape, and with the user exerting very little active force.

Two pivots, each with a fulcrum, are used to apply a self-created and controlled mild pivotal traction to the spine. If, for example, the user supports his back on the thoracic and lumbar support pivots, with the local center of gravity of the upper back on the upper side of the thoracic pivot and the local center of gravity of the lower back on the lower side of the thoracic pivot, then the intermediate region of the spine will be in a mild pivotal traction that aids in relieving back pain, improves posture, and aids in unloading and revitalizing the disks between the vertebrae. With minimal practice, the user can learn to vary the traction in the spine in a fully controlled manner from low to moderately high, and with a desired pattern of variation. The spinal traction is achieved by a single person, lying on the back in a safe position on a support surface such as the floor, and may be reached by even the elderly or the infirm. This approach permits the user to achieve the benefits of professional treatment in the home, without aid, and at low expense.

The pivots of the present invention are interactive postural devices formed of a firmly compliant material is used herein, a "firmly compliant" material is one that deforms as body weight is loaded there on, but does not deform to an extent that the described support function is lost. That is, the material is not hard and rigid in the manner of wood or hard plastic, so as to be uncomfortable against the body. On the other hand, the material is not so compliant that the body weight deforms the pivot to the extent that its loses its ability to support the portion of the body in contact with the pivot.

The preferred material of construction of the pads is a self-skinning foam that can be formed in closed molds of the desired shape, with the pads removed upon hardening of the foam. In a preferred approach, the foam i s formed by mixing together and curing an isocyanate and a resin/polyol. The compliance and firmness of the pivot may be controllably adjusted by varying the amounts and ratios of the reactants used.

It will be appreciated that the pivots, pads, and procedure of the present invention provide an important advance in permitting the low-cost continuation of professional treatment, and a regimen of training and conditioning, for the spine, ribs, back, and skull. Treatment is achieved with the spine in an unloaded or mildly loaded state, in a manner that is safe for use by the widest variety of persons. Other features and advantages of the invention will be apparent from the following more detailed description of the preferred embodiment, taken in conjunction with the accompanying drawings, which illustrate, by way of example, the principles of the invention.

BRIEF DESCRIPTION OF THE DRAWINGS

FIG. 1 is a side elevational view of three of the pivots of the invention in relation to their use by a person;

FIG. 2 is a perspective view of the lumbar support pivot;

FIG. 3 is an exploded perspective view of another embodiment of the lumbar support pivot having a removable support;

FIG. 4 is a perspective view of another embodiment of the lumbar support pivot, with inflatable interior bladders shown with phantom lines;

FIG. 5 is an end elevational view of another embodiment of the lumbar support pivot having a support strap;

FIG. 6 is a perspective view of the thoracic support pivot;

FIG. 7 is a perspective view of a pressure intensifying padb useful in conjunction with the thoracic and other pivots of the invention;

FIG. 8 is a side elevational view of a person applying traction to the spine utilizing the thoracic and lumbar support pivots;

FIG. 9 is a another embodiment of the thoracic support pivot with a symmetric structure;

DETAILED DESCRIPTION OF THE PREFERRED EMBODIMENTS

Figure 10:
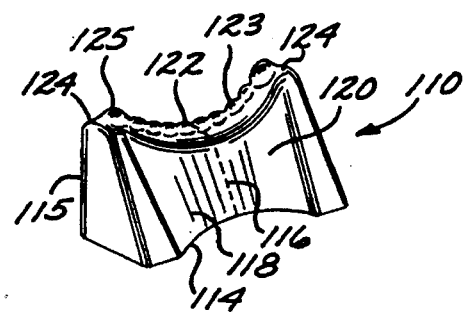
FIG. 10 is a perspective view of the occipital support pivot.

The present invention provides pivots and pads that are useful in supporting various parts of the human back, spine, ribs, and associated structure, and it is useful to first describe the relevant portions of the structure of the body. The terms are used herein in their conventional anatomical senses, unless stated to the contrary. The body may be generally considered to have a trunk including a spine running longitudinally along the center of the back. The longitudinal direction as used herein is that direction generally parallel to the spine and extending from head to toe. The lateral or transverse direction is perpendicular to the spine in the direction parallel to the line running from shoulder to shoulder of the person.

The spine is the central column to which other anatomical structure is connected. The spine is formed of a number of vertebrae connected together, so that the spine, when viewed as a whole, has a characteristic shape. It the upper end of the trunk, the head is supported on the portion of the spine extending above the trunk, and in particular the skull is connected to the spine. The ribs, collarbone, pelvis, and various muscles connect directly or indirectly to the spine.

The spine normally has about 32–34 vertebrae, which are conventionally divided into groups indicative of the associated region of the body for descriptive purposes. At the top of the spine are 7 cervical vertebrae, with the skull fused to the topmost or first cervical vertebra. The lateral sides of the skull in the occipital region near the connection to the first cervical vertebra are concavely shaped. The cervical vertebrae support the neck. Taken as a group, the cervical vertebrae assume a mildly concavely shaped form in the longitudinal direction (parallel to the overall length of the spine). The lateral sides of the neck are concavely shaped.

The upper portion of the trunk of the body is termed the thorax, and the corresponding portion of the spine is formed by 12 thoracic vertebrae, to which the ribs are connected. In general terms, the trunk is cylindrically shaped with a flattened back having the spine recessed in the center thereof, and the ribs curve outwardly from the spine to help define the shape of the trunk. In the longitudinal direction parallel to the spine, the thoracic vertebrae together have a mildly convex outward shape. If one runs a finger longitudinally along the spine, a series of small bumps are felt. These bumps are termed the spinal processes, and correspond to the shapes of the underlying individual vertebrae. In the upper portion of the back of the thorax, spaced about two inches to either side of the spine, are the scapulae or shoulder blades, which form part of the mechanism by which the arms are moved.

Below the thorax is the lumbar portion of the trunk, having 5 lumbar vertebrae, with the first lumbar vertebra connected to the twelfth thoracic vertebra. The lumbar portion of the spine is the portion commonly called the "small" of the back, and is longitudinally concavely curved inwardly. This curvature, also called lordosis, together with the curved shape of the thoracic vertebrae, defines the posture of the person to a great extent. In the lumbar region, the trunk has the same general shape as described above with a flat back, except as noted.

Below the lumbar region is the sacral region, having 5 sacral vertebrae. The pelvis, which provides the connection to the trunk for the legs, is connected to the sacral vertebrae. The longitudinal shape of the sacral vertebrae taken as a whole is slightly convex but continuous with the concave curvature of the thoracic spine, to bring the overall shape of the spine back to a generally very mild curvature.

At the lower end of the sacrum is the coccyx, commonly called the "tailbone", which is formed of three to five vertebrae fused together. Taken together, the lowest of the sacral vertebrae and the coccyx are generally flat in profile.

As a person ages, particularly if the person sits a great deal, the body tends to pull forwardly into a hunched position that semi-permanently deforms the spine and posture from their norms. The rest of the body, including the associated skeletal and muscular structure, adjust their positions somewhat to attempt to maintain the proper upright posture, leading to structural irregularities and imperfections because of the need to adjust from the normal positions. These changes to the body contribute to back pain and more serious back problems in later life. A principal purpose of the present invention is to provide apparatus that permits conditioning of the body to avoid these problems, and treatment of the problems when they do occur. Although there have been various types of apparatus to condition and treat other parts of the body, there has been relatively little attention paid to conditioning of the back, spine, and related structure to avoid back problems.

In many aspects, the present invention provides pads of particular shapes that have been designed to provide conditioning and/or therapy to particular parts of the spinal structure. In most cases, these pads are used with the person lying on the back, with the spine unloaded. In a few cases, the pads are used with the person lying on the front or in a sitting position, since the conditioning or treatment requires that position. Some of the pads are termed "pivots", because their shape includes a fulcrum which shapes the supported part of the body and permits particular types of exercises that have been found beneficial.

FIG. 1 illustrates the manner in which several of the pivots of the invention are placed relative to a person using them. A person 20 lies with the back 22 down on a horizontal support surface 24. Placement of the person on the back causes the spine of the person to be in a mostly unloaded condition, where there is little if any overall compressive force generated by the weight of some other portion of the body carried by the spine. The unloaded position of the spine is useful in treating various problems with the spine, because corrective pressures and techniques can be introduced without the need to overcome external loadings. Also, the supine position is a generally comfortable, relaxing one for most persons. One or more pivots are placed between the back 22 and the support surface 24, at the locations to be described. In most instances either from one to three pivots are used at any time, but to illustrate the positioning and relative positioning of the pivots, three pivots are shown in their positions of use in FIG. 1.

A lumbar support pivot 30 is placed under the lumbar region 32 of the back 22 of the person 20. As illustrated in FIG. 2, the lumbar support pivot 30 is a pad having a generally flat bottom 34 that rests upon the support surface 24. The pivot is laterally symmetric about a centerline 36. At a first end 38 of the pivot 30, positioned nearest the lumbar region and ribs, a lumbar support surface 42 is longitudinally inclined upwardly from the bottom 34 to a high point or fulcrum 44, which fits to the lordotic portion of the spine, as it should properly be shaped. The surface of the pivot 30 then is inclined longitudinally downwardly from the fulcrum to form the sacral support surface 45, meeting the bottom 34 at a second end 40 of the pivot 30.

The lumbar support surface 42 is generally flat to match the shape of the thoraco-lumbar region, although it is slightly dished on each side of the centerline 36 to conform to the slight lateral convex shaping of the back at that point. The sacral support surface 45 is generally flat but slightly concave in the longitudinal direction, and slightly dished or concave in the lateral direction, to conform to the sacral region of the lower back. The lateral sides of the fulcrum 44 slope downwardly and then flatten, as may be seen most clearly in FIG. 5, to join to the side supports to be described next. The fulcrum 44 thus acts as such in both longitudinal and lateral movements.

From each lateral margin of the sides of the fulcrum 44 and each lateral margin of the lumbar support surface 42, the upper surface of the pivot 30 is contoured upwardly to form side support surfaces 46. The contour of the surfaces 46 is shaped to match the concave curvature of the sides of the trunk, when the body of the person rests upon the pivot 30 with the lordotic region on the fulcrum 44. The side support surfaces 46 extends upwardly and outwardly from the central body of the pivot 30, and provide lateral support for the pelvis of the person using the pivot 30. Extending longitudinally along the centerline 36 of the fulcrum 44, the upper surface of the pivot 30 has a central spinal depression 48 that conforms to the spine of the person using the pivot 30 and in particular to the spinous processes, thereby permitting the person to lie comfortably on the pivot 30 without undue pressure on the spinous processes.

Several modifications to the pivot 30 are illustrated in FIGS. 3–5 and 17. In FIG. 3, the pivot 30 includes a recess 50 in the region of the fulcrum 44, which receives a conforming support pad 52, shown in FIG. 3 as removed from the recess. The support pad 52 can be inserted into a separate pouch (not shown) and used for a variety of support functions where the user is walking about. The pad 52 is preferably generally rectangular in shape with an apex at either end to conform to the shape of the upper surface of the pivot 30. The pad 52 is held in place in the recess 50 by a velcro patch 54 or other acceptable means.

FIG. 4 illustrates in phantom lines a pair of interior air bladders 60 within the pivot 30, placed below and on each side of the fulcrum 44, and extending laterally outwardly toward the side support surfaces 46. A fill tube 62 with closure extends from each bladder 60 to the exterior of the pivot 30, so that the bladder 60 may be manually inflated by the user. The closure may include a releasable check valve so that air can flow inwardly only, to inflate the bladder until manually released. Alternatively, there may be provided an air transfer tube 63 to transfer air between the bladders 60. The bladders 60 permit the height of the fulcrum 44 and/or the lateral supports 46 to be increased symmetrically or asymmetrically, providing a higher support surface for the lumbar or lordotic regions. This adjustability feature is supplied in the lumbar pivot 30, and the other pivots of the invention, because it permits the shape of the pad to be tailored to the body shape and treatment of the person 20. It is found that, as treatments using the pivots of the invention progress, the person normally can tolerate and benefit from an increasing height of the pads. The bladders 60 also are useful in performing certain exercises using the pivot 30, as will be described.

Yet another embodiment of the pivot 30 is illustrated in FIG. 5. The pivot 30 may be provided with strap attachment points 64 on either side near the bottom 34. Straps 66 are attached to these points 64. The straps 66 are of a length sufficient to be buckled around the lower trunk of the person 20 to provide a portable lumbar support. The support is rather bulky, and normally would not be worn out of the home or place of treatment. Instead, the removable pad 52 would be used when greater mobility is required. The pivot 30 when strapped in place permits the user to sit in chairs and move from place to place while enjoying the therapeutic benefits of the pivot 30 and the sense of lateral support that the side support surfaces 46 of the pivot 30 provide.

Figure 17:
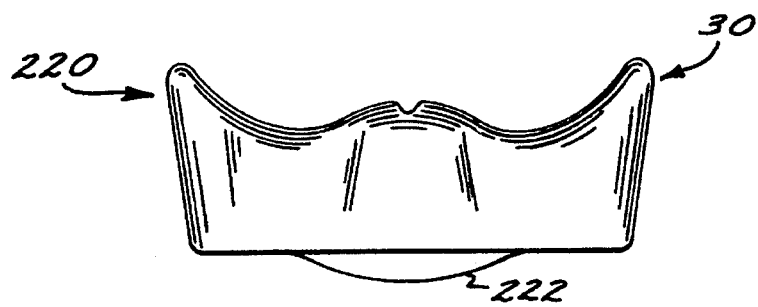
FIG. 17 is a perspective view of a pivot with a rounded rocker bottom.

A rocking pivot 220, which is depicted as a modification to the form of the pivot 30, is shown in FIG. 17. The pivot is similar in shape to the pivot 30, but has a curved bottom 222 rather than the flat bottom previously depicted in relation to FIGS. 2–5. The curved bottom 222 permits the person lying on the pivot 220 to perform rolling exercises in which the person rolls from side to side and end to end, over the curvature of the bottom 222. The height and curvatures of the bottom 222 can be varied as desired for a range of rolling movements. The bottom 222 may be made of the same material as the pivot itself, or a different material to achieve a particular effect. The use of a curved bottom has been illustrated for the lumbar pivot 30, but the thoracic pivot, cervical pivot, and occipital pivot can also be provided with curved bottoms for the same reasons.

The pivot 30 has many uses, the most common being to mobilize joints in the spine and pelvis, to apply a mild pivotal therapy to the spine, to improve the posture of the person, and to improve the strength and flexibility of muscles. The pivot 30 may be used in a completely passive manner, wherein the person 20 does no more than lie upon the pivot 30 in a correctly positioned location. This use of the pivot 30 is beneficial, because it helps to correct improper lordotic spinal curvature that develops in most persons, particularly those in sedentary occupations. The pivot 30 forces the thoraco-lumbar portion of the spine back into the proper shape. Thus, simply lying on the properly positioned pivot 30 for a half-hour while watching television, without any movement, is beneficial. The supported portion is reshaped to the proper lordotic curvature, while the spine is in the unloaded state. The reshaping aids the disks between the vertebrae to return to their correct shape and position, and to be nourished with the proper blood supply. After even such a passive treatment, the person feels refreshed.

The pivot 30 also permits the user to perform an active program of self-therapy to mobilize joints and improve strength and flexibility of muscles in the lower trunk and back. By rolling from side to side or in a forwards and backwards pattern over the fulcrum 44 (with either a flat or curved bottom), the person causes joints to move and muscles to work and stretch to increasing ranges of movement, all while the spine is unloaded and the back is biased to the correct slightly lordotic shape. This ability to perform exercises while maintaining the back in the proper posture is an important benefit. These passive and mildly active treatments can be used by persons who cannot perform other types of activities, such as the aged and the infirm, without danger to the user such as falling. Where present, the bladder 60 plays a role in active therapy. The bladder deforms as the person rolls to the side where the bladder is located, varying the deformation characteristic of the pad. If the transfer tube 63 is provided, air can flow from the bladder having the higher pressure to the bladder having the lower pressure. Pivots 30 having bladders can be manufactured with the bladders at a variety of locations, to provide different types of effects.

Finally, a physical therapist can use the pivot 30 in a program of therapy applied to the body of the person, such as the movement of joints to increase their mobility beyond what the person could do without aid. As the person becomes more mobile and able to take more treatment, the range of treatment can be increased by increasing the height of the fulcrum, inflating the bladders, or using a pivot made of less compliant material.

In using the lumbar support pivot 30, the side support surfaces 46 play an important part. For a person who does no more than lie on the pad, the side support surfaces 46 give a heightened sense of security of position, so that the person does not feel as though he or she will roll off the pad. For a person who performs active exercises, the surfaces 46 assist in performing the exercises. As the person rolls the hips and pelvis over the fulcrum 44 and toward one side, the side support surfaces first increasingly resist the movement to give a sense of restraint and positioning, and then assist in returning to the central position by providing a restoring force that pushes the hips upwardly as the hips are rolled back toward the fulcrum. There is also the positional feeling of containment, adding to the pleasure of the user as the pivot is used. Since a contemplated use of the pads of the invention is in a long term program of conditioning, providing such comfort is an important feature of the pivot.

Referring again to FIG. 1, a thoracic support pivot 70 is placed under a thoracic region 72 of the back 22 of the person 20. Is illustrated in greater detail in FIG. 6, the thoracic support pivot 70 has a generally flat bottom 74 (which could be curved, as previously discussed) that rests upon the support surface 24. The pivot 70 is laterally symmetric about a centerline 76. Along the centerline, an upper support surface 82 is longitudinally sloped upwardly from the bottom 74 at a first end 80 of the pivot 70, reaching a high point or thoracic fulcrum 84. The surface of the pivot then slopes longitudinally downwardly from the fulcrum 84 to form a lower support surface 83 that meets the bottom 74 at a second end 78. A side surface 85 slopes laterally downwardly from the centerline 76 to meet the bottom 74, so that the fulcrum 84 is operable as such in both the longitudinal and lateral directions.

The contour of the upper support surface 82 of the pivot 70 does not conform to the shape of the back, and instead slopes downwardly so as not to contact the upper lumbar region of the person, when the person lies with the fulcrum 84 in the central lumbar region. The lower support surface 83 of the pivot 70 follows the shape of the lower thoracic region into the thorace-lumbar transition to the lumbar region, particularly when the back is supported on the pivot 70 and is slightly arched. The pivot 70 has a shallow depression 86 running along the centerline 76 to comfortably fit the anatomy of the back at and adjacent to the spine, and in particular to receive the spinous processes.

The fulcrum 84 of the thoracic support pivot 70 is relatively narrow in the lateral direction. In particular, the pivot 70 at its top has a width less than the width between the scapulae or shoulder blades of the user. For most persons, this width is about 4 inches. This relatively narrow width ensures that the thoracic spine of the user will be supported along the lateral margins of the thoracic vertebrae and related musculature, and not by the shoulder blades, while resting in the supine position on the support surface 24. One objective of the use of the thoracic support pivot 70 is to support the person 20 from the thoracic region at and adjacent to the spine. This support permits the weight of the lateral portions of the chest to force the lateral sides of the back downwardly, stretching the ribs and related musculature at the breastbone joint that otherwise may tend to be drawn forward in a slumped posture. Alternatively, the user may lie on the stomach on the support surface with the thoracic pivot 70 under the sternum or breastbone, to mobilize the rib attachments along the spine in much the same manner.

The pivot 70 may be modified in several ways. As shown in FIG. 6, there may be provided an inflatable bladder 88 and external fill tube 90. The bladder 88 may be inflated to increase the height of the fulcrum 84 as needed for a particular person or type of exercise. A single bladder 88 is illustrated in FIG. 6 for the pivot 70, and a pair of bladders 60 is illustrated in FIG. 4 for the pivot 30. However, for any of the pivots, one or more than one bladder may be provided, and the bladders may be positioned in any manner desired. The pivot 70 may also be provided with a curved bottom to facilitate rolling exercises.

A movable pressure pad 92 modification is illustrated in FIG. 7, and as used with the pivot 70 in FIG. 6. The pad 92 is made of plastic or foam with a degree of rigidity as needed. Its shape may be varied widely, and as illustrated has the shape of a human thumb. It has a flat bottom 94 covered with a layer 96 of a weak pressure sensitive adhesive. (Other fastening approaches such as a pin extending downwardly from the bottom 94 or velcro patches can also be used where preferred.) The pad 92 is removably adhered to a selected location on the pivot 70, or it may be used in conjunction with any of the other pivots of the invention. The pad 92 protrudes outwardly from the otherwise more compliant pivot to which it is attached, to provide a relatively harder pressure point that contacts a selected region of the back of the user. The pad 92 provides the mechanical analog of a thumb or finger of a masseuse that achieves relief from pain by pushing hard against a tight muscle or joint. A similar pad having a flat, palm-like shape, is shown at numeral 98 in FIG. 6. Thus, the user of the present invention can apply self-directed intense pressure against particular regions, without needing aid by another person, after the user has been instructed on its application by a professional therapist. The pads 92 and 98 can be used singly or in a combination of several such pads, and can be readily positioned and repositioned as necessary.

The pivots of the invention may be used in pairs (or greater numbers, as three or four pivots together) to induce mild spinal traction, in the manner illustrated in FIG. 8. With the person 20 lying on the back in the supine position, two of the support pivots are used to create a spinal traction. The selected pivots are those that are normally adjacent to each other in the progression along the spine, as for example the thoracic support pivot and the lumbar support pivot. Since the greatest expected use of the pivots in pairs is expected for easing pain in the lower back, the use of the thoracic support pivot 70 and the lumbar support pivot 30 is illustrated in FIG. 8.

To apply a mild pivotal traction to the lower spine, the person 20 lies in the reclining supine position on the support surface 24, with the thoracic region 72 supported above the surface 24 on the thoracic support pivot 70, and the lumbar region 32 supported above the surface 14 on the lumbar support pivot 30. The thoracic support pivot 70 is positioned by the person so that the fulcrum 84 of the thoracic support pivot 70 is between the center of gravity of the supported lumbar region and the lumbar support pivot 30. The weight of the upper part of the person's body tends to cause the upper portion to pivot about the fulcrum 84 (in the counterclockwise direction in the view of FIG. 8). Similarly, the lumbar support pivot 30 is positioned by the person so that the fulcrum 44 of the lumbar support pivot 30 is between the center of gravity of the supported lumbar region and the thoracic support pivot 70. The weight of the lower part of the person's body tends to cause the lower portion to pivot about the fulcrum 44 (in the clockwise direction in the view of FIG. 8).

The pivoting of the upper body about the fulcrum 84 and the pivoting of the lower body about the fulcrum 44 are in different rotational directions, placing the intermediate region of the spine (in the lower back) into a mild pivotal traction. The traction is achieved with the person lying passively, except for minor shifting of position to induce the desired amount of traction. The person is in a safe position where injury is unlikely, and the magnitude of the traction is limited by the mechanical moments about the two fulcrums, which is not large. Nevertheless, experience has shown that the spinal traction induced by this technique can have significant conditioning and therapeutic effects in improving the general health of the back and in relieving pain and discomfort that would otherwise go untreated until the next visit to the office of the professional.

The person can gain additional pivotal mobility to enhance the pivotal traction by sliding the pivots 30 and 70 over the surface 24, while lying on the pivots. Additionally, if one or both of the pivots has a curved rocker bottom, a rolling motion can be induced to further mobilize the spine.

A variation of the thoracic pivot is the limited area support pivot 100, illustrated in FIG. 9. The pivot 100 is generally shaped in the manner of the thoracic support pivot 70, but is longitudinally symmetric from end to end. The pivot 100 is normally used by placing it at the point of maximum convexity of the spine, to support that small area only. The thoracic pivot 70 differs in that it is contoured to conform to the thoracic region of the back to achieve support over a broader area.

An occipital support pivot 110 is placed under the occipital region 112 of the back of the head or skull of the person 20. The occiput is found at the lower portion of the back of the skull, and is of particular interest because a number of muscles of the neck are joined to the skull in the occipital region. Some common disorders such as tension headaches arise in the occipital region because of tightness in these muscles. Persons who suffer from such headaches will be aware that a massaging of the occipital region and the upper neck can bring temporary relief from such headaches. A muscle that is massaged or pressed laterally does not normally remain contracted and tense. However, it is impractical to continue the massage for extended periods of time until the tension is fully relaxed. The occipital support pivot 110 can aid in relaxing the muscles and the person using the pivot, whether or not there is a headache.

As illustrated in FIG. 10, the occipital support pivot 110 has a generally flat bottom 114 that rests upon the support surface 24. An upper surface 115 (hidden in FIG. 10) slopes steeply upwardly from the bottom 114 to form the front of the pivot 110. Along a longitudinal centerline 116 of the pivot 110, at a lowest end 118 nearest the neck of the person, a lower surface 120 of the pivot 110 slopes downwardly to meet the bottom 114. Intermediate the upper surface 115 and the lower surface 120 is a raised fulcrum 122.

Extending laterally from both sides of the centerline 116, the surface of the fulcrum 122 slopes upwardly to form raised lateral supports 124. The upward slope of the fulcrum 122 as it forms the lateral supports 124 conforms to the curvature of the occiput, to provide good lateral support for the head as it rests upon the pivot 110. In the preferred embodiment, there are a number of small fingerlike protrusions 123 in the form of small knobs that extend upwardly from the surface of the fulcrum 122 along its entire length from side to side. At the upper lateral extreme of the fulcrum 122 are enlarged protrusions 125. The smaller protrusions 123 fit against the base of the occipital region where a number of small muscles called the suboccipital muscles join the occiput, and press against those muscles. The larger protrusions 125 are positioned to press against the upper end of the sternocleidomastoid muscle on either side of the neck, near its upper end where it attaches to the skull.

These protrusions 123 and 125 are made of a compliant material, and aid in focussing pressure on areas of pain, without causing undue discomfort to the user as would be the case if the protrusions were rigid. When the user rests his head upon the pivot 110 with the body in a relaxed position, the pressure from the protrusions 123 and 125 upon these muscles acts to reduce their contraction, thereby relieving the tension in them. The beneficial effect can be enhanced by moving the head to roll the occiput over the fulcrum 122, thereby massaging the muscles with the protrusions 123 and 125. The massaging action produced when the head is rolled about while in contact with the protrusions has been found to be beneficial in relieving tension headaches without use of drugs.

Figure 11:
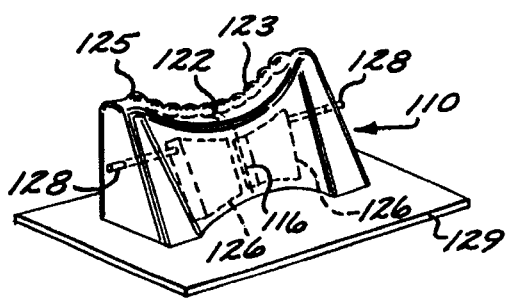
FIG. 11 is a perspective view of an alternative embodiment of the occipital support pivot, with inflatable bladders shown in phantom lines.

Another embodiment of the occipital support pivot 110 is illustrated in FIG. 11. This embodiment is generally similar in features to that shown in FIG. 10 and described previously, except that a pair of inflatable bladders 126, shown in phantom lines in the drawing, is provided within the body of the pivot 110, one laterally disposed from the centerline 116 on each side thereof. Each bladder 126 is inflated through fill tubes 128 that may be blown up by the user. In this manner, the upper surface of the fulcrum 122 may be raised and conformed more tightly to the neck of the user, and change the degree of deflection that the pivot 110 provides when placed between the occipital region 112 and the support surface 24. The pivot 110 of FIG. 11 is shown mounted on a flat base 129, to increase its stability.

Figure 16:
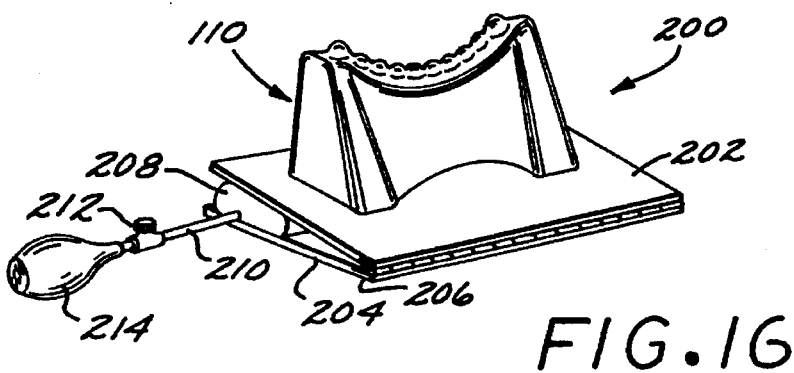
FIG. 16 is a perspective view of another embodiment of the occipital support pivot.

The massaging of the occipital region is enhanced by movement of the pivot 110. One approach to providing such movement is to curve the bottom of the pivot 110, in a manner analogous to that illustrated in FIG. 17. Another approach is illustrated in FIG. 16, a modified occipital pivot 200, which includes a structure like the pivot 110, is mounted on a movable base 202. The movable base 202 is pivotably joined to a stationary base 204 by a hinge 206. A mechanism to raise the movable base 202 is provided, preferably a bladder 208 positioned between the bases 202 and 204, so that inflation of the bladder 208 causes the pivot 110 to rise upwardly. The bladder 208 is filled through a tube 210 from an inflation bulb 214, operating through a valve 212. In one common use of the pivot 200, the bladder 208 is pumped full to raise the pivot 110 to its fullest height. The valve 212 is opened slightly so that the air in the bladder slowly leaks out, and the pivot 110 slowly returns to its lowest point. This exercise has been found to be particularly relaxing for the person supported on the pivot 200.

Figure 18:
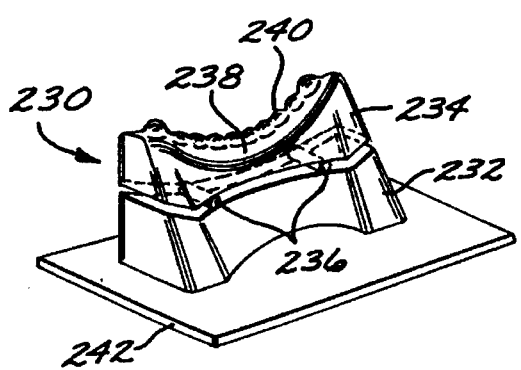
FIG. 18 is a perspective view of another embodiment of the occipital support pivot.
Figure 19:
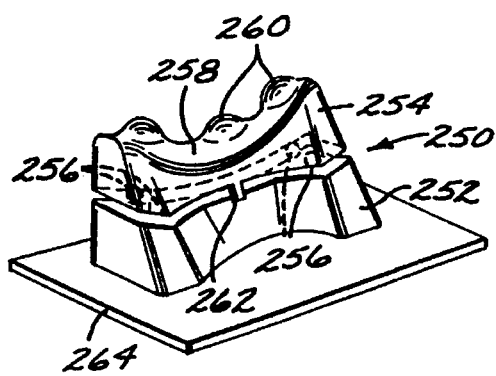
FIG. 19 is a perspective view of yet another embodiment of the occipital support pivot.

Rocking of the occipital support can be achieved with mechanical means, also, as illustrated in FIGS. 18 and 19. A laterally mobile occipital support pivot 230 includes a pivoting base 232 having a laterally curved upper surface and an occipital pivot 234 that rolls on the upper surface of the base 232 on roller bearings 296. The pivot 234 has the same general features as the pivot 110, including a fulcrum 238 and a plurality of protrusions 240. The entire structure is mounted on a stationary base 242 for stability. With the pivot 230, the person can roll the head from side to side on the bearings, to bring the protrusions 240 to bear on particular regions of the occiput. At the same time, the person can roll the head longitudinally over the fulcrum 238.

Another approach to increased movement of the pivot is illustrated in FIG. 19. A multiaxially mobile occipital support pivot 250 includes a pivoting base 252 having a longitudinally and transversely curved upper surface. An occipital pivot 254 rolls on the upper surface of the base 252 on ball bearings 256. The pivot 254 has the same general features as the pivot 110, including a fulcrum 258 and protrusions 260. In this case, the protrusions 260 are illustrated as three large, noncolinear knobs that are positioned to apply force to a limited number of areas of the occipital region. Such variations of the number and placement of the protrusions can be made with any embodiment of the occipital support pivot (and the cervical support pivot, to be described below). The pivot 250 includes a stationary base 264 that increases stability during use.

Since the pivot 254 is mounted to the base 252 on ball bearings 256, it can roll in both the lateral and longitudinal directions, or any combination of these directions. For some exercises, it may be desirable to limit the extent of rotation in one direction. In FIG. 19, a limiting post 262 extends from the lower side of the pivot 254, so that at some range of movement of the pivot 254, the post 262 engages the base 252 to prevent further movement in that direction. It that point, the person can apply a force to the head and neck to achieve traction, if desired. The post 262 is made adjustable and movable so that the limit of motion can be fixed by the person using the pivot 250.

(The occipital pivot 110 and its variations are placed under the occipital region 112. The placement of the pivot 110 is not shown in FIG. 1, because its placement is not compatible with the simultaneous use of the cervical support pivot, to be described next. The cervical support pivot performs many of the same functions as the occipital support pivot, and additionally supports the cervical region.)

Figure 12:
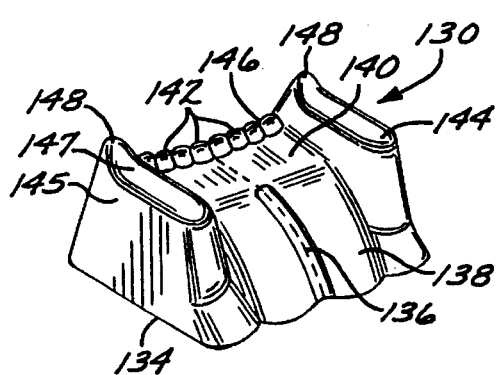
FIG. 12 is a perspective view of the cervical support pivot.

As illustrated in FIG. 1, a cervical support pivot 130 is placed under the cervical region 132 and occiput 112 of the skull of the person 20. Referring to FIG. 12, the cervical support pivot 130 has a generally flat bottom 134 that rests upon the support surface 24. At its upper end, which fits against the occiput 112, the structure of the cervical support pivot 130 is similar to that of the occipital support pivot 110. An upper surface rises from the bottom 134 to form the front of the pivot 130. Along a longitudinal centerline 136 of the pivot 130, at a lowest end 138 nearest the neck, a cervical support surface 140 of the pivot 130 tapers gradually downward and then more sharply downward to meet the bottom 134. Intermediate the upper surface and the cervical support surface 140 is a fulcrum 146. The fulcrum slopes gradually upwardly on each side of the centerline 136, and has a plurality of protrusions 142 thereupon. The gradually descending portion of the cervical support surface 140 follows the anatomical curvature of the lower portion of the back of the head and skull, and upper portion of the occiput, while the laterally upward curvature of the fulcrum 146 follows the lateral curvature of the occiput.

A lateral support 145 projects upwardly from each lateral margin of the fulcrum 146 and the cervical support surface 140. The top of the support 145 is a generally flat surface 147, having upwardly extending protrusions thereupon at either longitudinal end. At the lateral ends of the fulcrum 146 are a pair of first protrusions 148 that project upwardly to contact the sternocleidomastoid muscles in the region where they attach to the mastoid processes. The protrusions 148 aid in relieving stress in these muscles, particularly when the person rolls his head over the fulcrum 146.

Additionally, there is provided a pair of second protrusions 144 positioned at the other end of the surface 147, and raised a sufficient distance that they contact the upper trapezius muscle and first rib of the user, when the user rolls his head to the side where the particular protrusion 144 is located. Placement of the protrusions 144 and 148 on the top of the lateral support 145 provides stability for the protrusions, so that they need not be so long that they displace so much in use as to be ineffective in performing their role of massaging the contacted portions of the person. The combination of the protrusions 142, 144, and 148 provides a beneficial relaxing massage when the person rolls his head around on the fulcrum 146.

As indicated, any or all of the pivots 30, 70, 110, and 130 may be used singly or in groups to apply pressure to portions of the spinal column, the back, and the occipit, while the body is supported in part on the pivot. The magnitude of the supported body weight determines the force that may be applied to the fulcrum of the pad and related areas. Slight movement of the supported part of the body induces a massaging action in the affected body part.

The pivots 30, 70, 110, and 130 are used for the most part with the person in the supine position on the back. The pivots provide a pleasant relief and reposturing effect when used passively, and permit mobilizing and stretching movements when used actively. A person can use the pivots in an ongoing program of self-applied conditioning that improves mobility, strengthens muscles, improves posture, and provides relaxation. The pivots are also useful when employed by a therapist who is performing therapy upon the body of the person. The therapist utilizes the pivots in the manner described herein and otherwise, but is usually able to apply greater forces and mobilizations than possible when used by the person without aid. However, after learning the proper techniques from the therapist, the person can utilize the pivots in a self-therapy program between visits to the therapist.

As they progress in life, most persons who sit for extended periods develop a hunched posture that is evidenced in the aforementioned problems with the back and with posture, and also are evidenced in a gradual forward contraction and repositioning of the shoulders and frontal rib attachments. This movement is gradual over a period of years, but results in drastically reduced flexibility and mobility of the body, which in turn can lead to back pain as the body adjusts itself to respond to the gradual changes.

Figure 13:
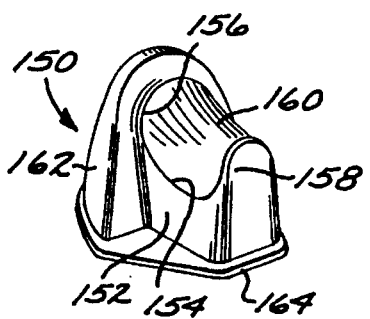
FIG. 13 is a perspective view of a stackable shoulder support pad.
Figure 14:
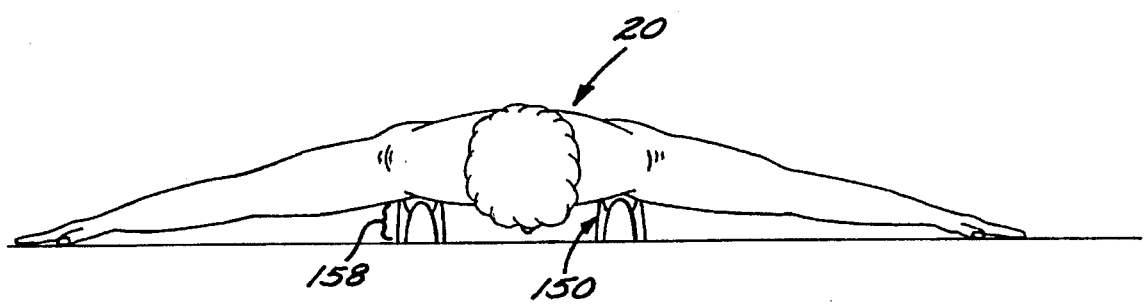
FIG. 14 is an end view of a person supported in the horizontal face down position on two of the shoulder support pads.

A pad structured in accordance with the invention is used to treat the frontal changes in skeletal and muscular structure, to aid in reducing the hunching effect. A shoulder support pad 150, shown in FIG. 13 and also sometimes termed a hand saddle, is used to support a person in a face-down position from the shoulders, as shown in FIG. 14. The pad 150 has a hollow, rigid plastic body 152 whose central surface 154 is generally U-shaped. Preferably, the two sides or legs of the U-shaped body are asymmetric, with a first leg 156 extending to a greater height than does a second leg 158. A compliant foam padding 160 fills the U-shaped region between the legs 156 and 158 above the surface 154. A rigid end piece 162 made of plastic and having a width greater than the width of the body 152 is integrally joined with the body 152 at the first leg 156. The body 152 is hollow and shaped such that the pads 150 are stackable one over the other, as may be done at numeral 158 of FIG. 14. Any number of pads can be stacked under each shoulder to achieve either symmetric or asymmetric support.

In one approach to using the pads 150 illustrated in FIG. 14, the person 20 lies on the stomach and stacks the pads 150 under each shoulder until his or her chest and sternum are raised off the surface 24. This support causes the shoulders to be pushed back relative to the chest, stretching the muscles of the chest and the rib attachments along the breastbone. It has been found that even relatively short periods of this treatment are quite beneficial in reducing tightness in the chest, and improving the flexibility of the chest.

Figure 15:
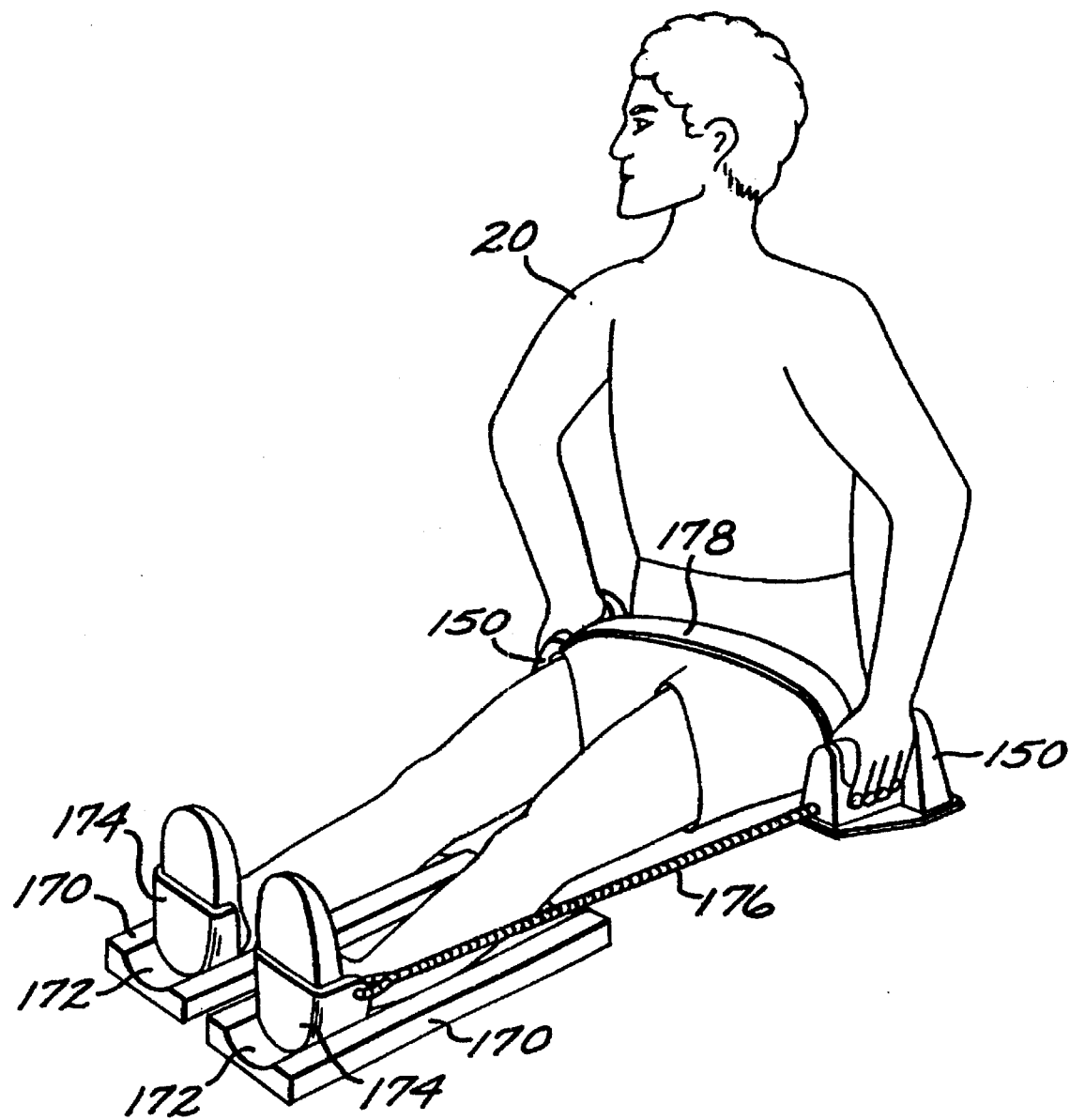
FIG. 15 is a perspective view of a person supported in a sitting position by pushing up on two of the shoulder support pads.

In another approach to using the pads 150 illustrated in FIG. 15, the person 20 sits upon the floor with the feet in guides 170 that have heel recesses 172 molded therein. Each foot is held in a stirrup 174. One of the pads 150 is placed adjacent the hips on either side of the body, and an elastic cord 176, such as a bungee cord, is stretched from the stirrup 174 to the pad 150. The person 20 can exercise the legs by raising the body off the floor by pushing downward on the pads 150, and moving the legs against the force of the cords 176. Optionally, a strap 178 can be attached to the pads 150 to extend across the body of the person 20. In this exercise, the person places his hands on the foam padding 156 and pushes downwardly to raise his torso up, strengthening his arms and chest with the spine in tension, and with the back in the proper upright position and posture. The strap 178, if present, increases the force that is applied. The shape of the pad 150, as previously described, is particularly comfortable to use in this sitting push up exercise.

All of the pivots 30, 52, 70, 92, 98, 110, and 130, are preferably made of a self-skinning foam material. The foam material is preferably prepared by mixing together a resin/polyol filler and an isocyanate catalyst, together termed the foam reactants, and permitting this mixture to react and harden. In a typical situation, the resin/polyol is present in an amount of about 70 parts by weight and the isocyanate is present in an amount of about 30 parts by weight. This materials system is available commercially from Poly Tech Industries, City of Industry, California, as product 10-12FR. Different densities of the foam can be prepared by increasing or decreasing the relative amount of the filler, and such other products are also available from the same manufacturer.

The self skinning foam has the characteristic that it expands to fill a volume provided, and the density of the foam is determined in part by the amount of the expansion of the foam to fill the volume. The smaller the amount of self skinning foam ingredients reacted in a volume, the lower the density and the more compliant the foam.

In practice, it has been found convenient to determine the amount of the foam reactants as follows. A closed mold of a particular size is prepared, as the design of the pivot requires. The mold is filled with a flowable solid such as rice, which is thereafter weighed. A standard medium density pad is prepared by providing an equal weight of reactant (that is, 1 part resin/polyol plus isocyanate for each part rice, by weight). A less dense, and therefore more compliant, pivot is made by using a lower ratio of the reactants, as 1 part reactant for each 2 parts rice, or even 1 part reactant for each 3 parts rice. A denser, and therefore less compliant, pivot is prepared by using a higher ratio of the reactants, as 2 parts reactant for each 1 part rice, or using the more dense foam reactants available from the manufacturer.

It is intended that pivots of a range of hardnesses will be prepared, because persons with very restricted mobility or with infirmities normally start therapy using soft pivots. As the body is reshaped and the person has adjusted to the use of the pivot, a less compliant pivot that gives more stringent treatment is substituted.

To mold the pivot, a split female mold is prepared. The inside surface of the mold is coated with a wax or silicone release agent by spraying. The mold is closed with a rubber gasket, and clamped shut. The mold has openable vents in the cover to permit the escape of trapped gases and excess foam material. The density of the foam and its compliance can be adjusted somewhat by opening the vents to permit escape of gas and foam material during manufacture.

The required amount of each reactant is mixed outside the mold. The two ingredients react exothermically, and as the temperature begins to rise the mixture is added to the mold. The mold halves are closed and clamped shut, and the vents are closed. These vents may be later opened to release gas pressure. The foam expands to fill the inside of the mold, and then cools back to ambient temperature. The pivot is then removed from the mold and set aside to complete curing. Approximately 80 percent of the ultimate hardness is achieved in about the first 15 minutes of reaction, and curing to full strength requires about another 24 hours at ambient temperature.

The present invention therefore provides an important advance in the art of therapy and preventive treatments. The use of the invention can give self treatments and condition the back to mobilize joints, reduce tightness of the musculature, apply a mild tension to the spine, and apply pressure to points of pain that can be relieved by mild pressure and gentle massage. Although particular embodiments of the invention have been described in detail for purposes of illustration, various modifications may be made without departing from the spirit and scope of the invention. Accordingly, the invention is not to be limited except as by the appended claims.

What is claimed is:

1. A shoulder support pivot system, comprising a body made of a rigid material in the form of a U having a first leg, a center, and a second leg, wherein the body is asymmetric with the first leg of the U extending upwardly to a height greater than the second leg of the U; and a compliant foam material filling the center of the U, the upper surface of the foam material extending longitudinally from the top of the first leg of the U to the top of the second leg of the U, the upper surface of the foam material further sloping laterally downwardly.

2. The pivot system of claim 1, further including:

an end piece of lateral width greater than the width of the body and joined to the body adjacent the first leg.

3. The pivot system of claim 1, further including:

an elastic cord having a first end and a second end, the first end being affixed to the body, and a foot stirrup affixed to the second end of the elastic cord.

4. The pivot system of claim 1, further including:

a strap having a first end and a second end, the first end being affixed to the body, and a second body made of a rigid material in the form of a U affixed to the second end of the strap.

5. The pivot system of claim 1, wherein the body is a hollow body, and wherein the pivot system further includes a second hollow body that is stackable within the hollow body, the second hollow body being made of a rigid material in the form of a U having a first leg, a center, and a second leg, wherein the second hollow body is asymmetric with the first leg of the U extending upwardly to a height greater than the second leg of the U; and a compliant foam material filling the center of the U of the second body, the upper surface of the foam material extending longitudinally from the top of the first leg of the U to the top of the second leg of the U, the upper surface of the foam material further sloping laterally downwardly.

* * * * *